United States Patent [19]

Seigneurin

[11] Patent Number: 5,125,838
[45] Date of Patent: Jun. 30, 1992

[54] ENDODONTIC CANAL INSTRUMENT MADE OF TITANIUM

[75] Inventor: Michel Seigneurin, Rioz, France

[73] Assignee: Micro Mega SA, Besancon, France

[21] Appl. No.: 635,534

[22] PCT Filed: Apr. 9, 1990

[86] PCT No.: PCT/FR90/00250

§ 371 Date: Jan. 8, 1991

§ 102(e) Date: Jan. 8, 1991

[87] PCT Pub. No.: WO90/14799

PCT Pub. Date: Dec. 13, 1990

[30] Foreign Application Priority Data

Jun. 5, 1989 [FR] France ................. 89 07570

[51] Int. Cl.⁵ ............................... A61C 1/02

[52] U.S. Cl. ................... 433/102; 433/165; 433/224

[58] Field of Search .............. 433/102, 165, 224, 225

[56] References Cited

U.S. PATENT DOCUMENTS 5,066,230 11/1991 Weissman ................... 433/102

FOREIGN PATENT DOCUMENTS 3620527 12/1987 Fed. Rep. of Germany ...... 433/102

Primary Examiner—Cary E. O'Connor
Attorney, Agent, or Firm—Weiser & Stapler

[57] ABSTRACT

Canal instrument used in endodontics, characterized in that its flexible blade is made at least partially of titanium or of titanium alloy.

4 Claims, No Drawings

ENDODONTIC CANAL INSTRUMENT MADE OF TITANIUM

The present invention relates to, as a new industrial product, a canal instrument used in endodontics.

There exist at present a good number of canal-type instruments which differ from one another in the shape of their blade, upon which their mode of operation depends. Some of these instruments are standardized, and for this reason manufacturers have little freedom of action in their search to improve these products.

In particular, one of the main problems to be solved consists in simultaneously combining a good and lasting cutting quality of these instruments with a high degree of flexibility allowing the instrument to work correctly in all the shapes of dental canals, some of which, as is known, are particularly tortuous. Now, in the case of the present-day instruments whose blades are generally made of stainless steel in the better makes, the lack of flexibility may lead to the point of the instrument not following the geometry of the canal, thus resulting in the formation of false canals.

Furthermore, it is known that, under poor conditions of use, a canal instrument may break in the canal and in some cases it is impossible to remove it, this representing a risk, given the possible effects of stainless steel trapped inside a root.

The aim of the present invention is to solve the above problems by providing an instrument with a very high degree of flexibility, which retains the cutting characteristics of the stainless steel or carbon instruments and which also, by virtue of the biocompatibility of its material, considerably reduces the risks of infection which can be caused by a fragment remaining in a canal.

According to the invention, this result is achieved with a canal instrument used in endodontics, characterized in that its blade is made at least partially of titanium or of titanium alloy.

In the case of a titanium alloy, those compositions will be preferred in which the titanium predominates.

A canal instrument of this type presents outstanding work capacities together with the utmost safety of use.

It can be sterilized without any problems.

I claim:

1. A canal instrument used in endodontics for preparing a root canal having curved portions, wherein the canal instrument has flexible blade portions formed at least partially of titanium.

2. The canal instrument of claim 1 wherein the titanium is formed as an alloy.

3. The canal instrument of claim 2 wherein the titanium alloy contains at least 50% titanium.

4. The canal instrument of claim 2 wherein the titanium alloy is predominantly titanium.

* * * * *